United States Patent [19]

Arend et al.

[11] 4,257,987

[45] Mar. 24, 1981

[54] LOWER ALKYL DI PROPARGYL PHOSPHATES

[75] Inventors: Günter Arend, Dormagen; Wolfgang Behrenz, Overath; Hans-Dieter Block, Cologne, all of Fed. Rep. of Germany

[73] Assignee: Bayer Aktiengesellschaft, Leverkusen, Fed. Rep. of Germany

[21] Appl. No.: 76,053

[22] Filed: Sep. 17, 1979

Related U.S. Application Data

[62] Division of Ser. No. 910,302, May 26, 1978, abandoned.

[30] Foreign Application Priority Data

Jun. 8, 1977 [DE] Fed. Rep. of Germany ....... 2727479

[51] Int. Cl.$^3$ .................... C07F 9/113; A01N 57/12; A01N 57/14; A01N 57/16
[52] U.S. Cl. .................................. 260/956; 424/219; 424/203; 424/211; 424/200; 424/217; 424/216; 424/212
[58] Field of Search .......................................... 260/956

[56] References Cited

U.S. PATENT DOCUMENTS 3,780,144  12/1973  D'alellio .............................. 260/956

FOREIGN PATENT DOCUMENTS 2406783  8/1974  Fed. Rep. of Germany ........... 260/956
526264  9/1972  Switzerland ............................. 260/956

*Primary Examiner*—Anton H. Sutto
*Attorney, Agent, or Firm*—Sprung, Felfe, Horn, Lynch & Kramer

[57] ABSTRACT

Synergistic arthropodicidal compositions containing (1) a phosphorus-containing compound of the formula

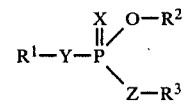

in which
 $R^1$, $R^2$ and $R^3$ each independently is an optionally substituted alkyl, alkenyl or aryl radical, at least one of $R^1$, $R^2$ and $R^3$ being an optionally substituted alkenyl radical unsaturated in the 2-position,
 X is oxygen or sulphur, and
 Y and Z each independently is oxygen, sulphur or a direct bond; and if both Y and Z are oxygen or sulphur or a direct bond, then any of $R^1$, $R^2$ and $R^3$ can denote propargyl in addition to the radicals indicated above, and (2) at least one (A) carbamate, (B) carboxylic acid ester, (C) phosphoric acid ester other than (1), (D) halogenocycloalkane or (E) halogenoalkane.

7 Claims, No Drawings

LOWER ALKYL DI PROPARGYL PHOSPHATES

This is a division of application Ser. No. 910,302, filed May 26, 1978, now abandoned.

The present invention relates to new arthropodicidal, especially insecticidal and acaricidal, synergistic combinations of certain phosphorus-containing compounds (some of which are known) and certain other, known, pesticidal active compounds.

It has already been disclosed that the following active compounds and groups of active compounds have pesticidal, in particular insecticidal and acaricidal, properties:

(A) carbamates, for example 2-iso-propyl-phenyl N-methylcarbamate, 2-(1-methyl-allyl)-phenyl N-methylcarbamate, 3-iso-propyl-4-methoxy-phenyl N-methylcarbamate, 2-[1,3-dioxolan-2-yl-phenyl]N-methyl-carbamate, 2,2-dimethyl-1,3-benzodioxol-4yl N-methylcarbamate, 2,2-dimethyl- or 2-methyl-2,3-dihydrobenzofuran-4-yl N-methyl-carbarate and 2,3-dihydro-2,2-dimethylbenzofuran-7-yl N-acetyl-N-methyl-carbamate, 3,4,5-trimethyl-phenyl N-methylcarbamate and 1-naphthyl N-methyl-carbamate;

(B) carboxylic acid esters, for example 2,3,4,5-tetrahydrophthalimidomethyl-chrysanthemate, acetic acid 2,2,2-trichloro-1-(3,4-dichlorophenyl)-ethyl ester and 3-phenoxybenzyl 2,2-dimethyl-3-(2,2-dichlorovinyl)-cyclopropanecarboxylate;

(C) phosphoric acid esters, for example O,O-dimethyl O-(2,2-dichlorovinyl) phosphoric acid ester and O,O-dimethyl O-[3-methyl-4-methylthio-phenyl]thionophosphoric acid ester;

(D) halogenocycloalkanes, for example hexachlorocyclone hexane; and (E) halogenoalkanes, for example 1,1,1-trichloro-2,2-bis-(4-methoxyphenyl)-ethane.

Furthermore, synergistic mixtures of carbamates, for example 2-iso-propoxyphenyl N-methylcarbamate, or of phosphoric acid esters, for example O,O-diethyl O-(2-isopropyl-4-methyl-pyrimidin-6-yl)phosphorothioate, or of naturally occurring or synthetic pyrethroids with piperonyl ethers, for example α-[2-(2-butoxyethoxy)-ethoxy]-4,5-methylene-dioxy-2-propyl-toluene, are known (see Bull. Org. Health Org. 1966, 35, pages 691–708; G. Schrader, Die Entwicklung neuer insektizider Phosphorsäureester (The Development of New Insecticidal Phosphoric Acid Esters) 1963, page 158; and W. Perkov, Die Insektizide (Insecticides), 1966, pages 516–524). The activity of these synergistic agents is not satisfactory; only α-[2-(2-butoxy-ethoxy)ethoxy]-4,5-methylenedioxy-2-propyl-toluene (piperonyl butoxide) has acquired a certain importance. Furthermore, the known synergistic agents can only be prepared in an involved and expensive manner, whereby their use possibilities are limited. The discovery of readily available and inexpensive synergistic agents is thus desirable.

The present invention now provides an arthropodicidal composition containing as active ingredients (1) a phosphorus-containing compound of the general formula

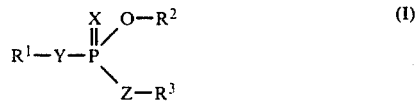

in which $R^1$, $R^2$ and $R^3$, independently of one another, each represents an alkyl, alkenyl or aryl radical, which can be optionally substituted, at least one of $R^1$, $R^2$ and $R^3$ representing an optionally substituted alkenyl radical which is unsaturated in the 2-position, X represents oxygen or sulphur and Y and Z, independently of one another, each represents oxygen, sulphur or a direct bond, and if both Y and Z represent oxygen or sulphur or a direct bond, $R^1$ and/or $R^2$ and/or $R^3$ can denote propargyl in addition to the radicals indicated above, and (2) at least one compound selected from (A) carbamates, (B) carboxylic acid esters (which expression includes the naturally occurring and synthetic pyrethroids), (C) phosphoric acid esters, (D) halogenocycloalkanes and (E) halogenoalkanes, alone or in admixture with a solid or liquid or liquefied gaseous diluent or carrier.

Surprisingly, the insecticidal and/or acaricidal action of the active-compound combinations according to the invention is considerably higher than the action of the individual components or of the sum of the actions of the individual components. Furthermore, it is considerably higher than the action of the active compound combinations, which are already known, of 2-isopropoxy-phenyl N-methyl-carbamate and piperonyl butoxide. In addition, the phosphorus-containing compounds of the formula (I) exhibit excellent synergistic activity not only with one class of active compound but with active compounds from the most diverse groups of chemical substances. Thus the synergistic mixtures according to the present invention represent a valuable enrichment of the art.

The preferred phosphorus-containing compounds of the general formula (I) are those in which $R^1$ represents alkyl with 1 to 4 carbon atoms or alkenyl with 2 to 4 carbon atoms, either of which can be substituted by halogen or alkoxy of up to 4 carbon atoms, or represents phenyl which can be substituted by halogen or alkyl with 1 to 4 carbon atoms, $R^2$ represents alkyl with 1 to 4 carbon atoms or alkenyl with 2 to 4 carbon atoms, either of which can be substituted by halogen or alkoxy of up to 4 carbon atoms, or represents phenyl, $R^3$ represents alkenyl with 3 to 4 carbon atoms, which carries a double bond in the 2-position and can be substituted by methyl, or represents alkyl of up to 4 carbon atoms, provided that at least one of $R^1$, $R^2$ and $R^3$ represents an alkenyl radical which is unsaturated in the 2-position (especially allyl), X represents oxygen or sulphur and Y and Z, independently of one another, each represents oxygen, sulphur or a direct bond.

In addition, compounds of the formula (I) in which both Y and Z represent oxygen or represent sulphur or represent a direct bond and $R^1$, $R^2$ and $R^3$ independently of one another represent propargyl, in addition of the meanings indicated above, are preferred.

Preferred carbamates (A) are those of the general formula

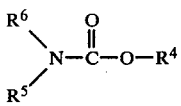 (II)

in which
R$^4$ represents aryl, a heterocyclic radical or an oxime radical,
R$^5$ represents hydrogen or alkyl with 1–4 carbon atoms and
R$^6$ represents alkyl with 1 to 4 carbon atoms, alkylcarbonyl with 1–6 carbon atoms in the alkyl radical [which can be optionally substituted by hydroxyl or methylthio] or the radical —S—W,
wherein W represents an aliphatic radical with 1 to 4 carbon atoms [which is optionally substituted by halogen] (especially CCl$_3$ or CF$_3$), or an aryl radical (especially phenyl) [which is optionally substituted by (preferably) CN, halogen (especially chlorine), methyl, trihalogenomethyl, trifluoromethylmercapto or NO$_2$], or methoxycarbonyl or the radical V—SO$_2$—N—R$^5$, wherein V represents alkyl or halogenoalkyl with 1–4 carbon atoms, or an aryl (preferably phenyl) radical [optionally substituted by halogen, trihalogenomethyl, CN, methyl or nitro].

Particularly preferred carbamates (II) are those in which R$^4$ represents phenyl or naphthyl [either of which is optionally substituted by alkyl, alkenyl, alkoxy or alkylmercapto with up to 5 carbon atoms in each case, dialkylamino or dialkenylamino with up to 3 carbon atoms per alkyl or alkenyl part, halogen (especially chlorine), dioxolanyl or the radical —N=CH—N (C$_{1-4}$-alkyl)$_2$].

Other particularly preferred carbamates (II) are those in which R$^4$ represents 2,3-dihydrobenzofuranyl, benzodioxole, benzothienyl, pyrimidyl or pyrazolyl [each of which is optionally substituted by C$_{1-4}$-alkyl (especially methyl) or dialkylamino with 1 to 4 carbon atoms per alkyl part].

Yet other particularly preferred carbamates (II) are those in which R$^4$ represents an oxime radical of the general formula

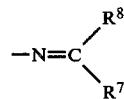 (IIa)

in which
R$^7$ and R$^8$, which may be identical or different, each represent alkyl, alkenyl, alkynyl, alkoxy, alkylmercapto, alkoxycarbonyl, carbonylamide or alkylmercaptoalkyl with up to 5 carbon atoms in each case, cycloalkyl with 3 to 7 carbon atoms, CN, aryl (especially phenyl), aralkyl with up to 5 carbon atoms in the alkyl moiety, an optionally substituted heterocyclic radical or alkyl with up to 5 carbon atoms and substituted by a heterocyclic radical, or
R$^7$ and R$^8$ together represent a dioxolanyl or dithiolanyl radical which is optionally substituted by C$_{1-4}$-alkyl.

Preferred carboxylic acid esters (B) are those of the general formula

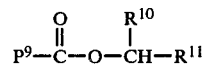 (III)

in which
R$^9$ represents alkyl, aralkyl, aryl or cycloalkyl, each of which can be optionally substituted,
R$^{10}$ represents hydrogen, alkyl, halogenoalkyl, alkenyl or alkynyl of up to 4 carbon atoms, or CN and
R$^{11}$ represents aryl or a heterocyclic radical, or
R$^{10}$ and R$^{11}$ together form an optionally substituted cyclopentenone ring.

Particularly preferred carboxylic acid esters (III) are those in which
R$^9$ represents alkyl with 1 to 6 carbon atoms [which is optionally substituted by optionally halogen-substituted phenyl], cyclopropyl [which is optionally substituted by alkyl, alkenyl, halogenoalkyl or halogenoalkenyl with up to 6 carbon atoms in each case] or phenyl [which is optionally substituted by halogen], and/or
R$^{10}$ represents hydrogen, alkyl with 1 to 6 carbon atoms, halogenoalkyl with 1 to 4 carbon atoms and up to 3 halogen atoms, CN or ethynyl, and/or
R$^{11}$ represents phenyl [which is optionally substituted by C$_{1-4}$-alkyl, halogen (especially fluorine or chlorine), optionally halogen-substituted or methyl-substituted phenoxy or optionally substituted benzyl], furanyl, tetrahydrophthalimido or benzodioxole [any of which is optionally substituted by halogen (especially chlorine), alkyl or alkenyl with up to 4 carbon atoms or benzyl] or cyclopentenone [which is optionally substituted by C$_{1-4}$-alkyl, furfuryl or C$_{2-5}$-alkenyl].

The naturally occurring pyrethroids are also particularly preferred.

Preferred phosphoric acid esters (C) are those of the general formula

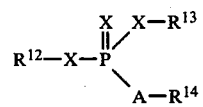 (IV)

in which
each X, independently of any other, represents O or S,
A represents O, S, —NH— or a direct bond between the central P atom and the radical R$^{14}$,
R$^{12}$ and R$^{13}$, which may be identical or different, each represent alkyl or aryl and
R$^{14}$ represents alkyl, aryl, heteroaryl, aralkyl, alkenyl, dioxanyl or an oxime radical or represents a radical identical to that to which it is bonded [with the proviso that R$^{14}$-A- should not denote the 2-methoxy-4-cyano-phenoxy radical when chloromethanephosphonic acid dipropargyl ester is the synergistic agent of the formula (I)].

Particularly preferred phosphoric acid esters (IV) are those in which
R$^{12}$ and R$^{13}$, which may be identical or different, each represent C$_{1-4}$-alkyl or phenyl, and
R$^{14}$ represents alkyl with 1–4 carbon atoms [which is optionally substituted by halogen, CH, CN, optionally halogen-substituted phenyl, carbonylamide, or sulphonylalkyl, sulphoxyalkyl, carbonylalkyl, alkoxy, alkylmercapto or alkoxycarbonyl each with up to 5 carbon atoms], alkenyl with up to 4 carbon atoms [which is optionally substituted by halogen, optionally halogen-substituted phenyl or alkoxycarbonyl with up to 5 carbon atoms], or an oxime radical of the general formula

wherein
R$^7$ and R$^8$ have the meaning indicated above (especially cyano or phenyl) or R$^{14}$ represents dioxanyl, which is substituted by a radical identical to that to which R$^{14}$ is bonded, or R$^{14}$ represents a radical identical to that to which it is bonded or R$^{14}$ represents phenyl [which is optionally substituted by methyl, nitro, CN, halogen or methylmercapto], or R$^{14}$ represents a hetero-aromatic structure (such as pyridine, quinoline, quinoxaline, pyrimidine, diazinone or benzo-1,2,4-triazine) which is optionally substituted by C$_{1-4}$-alkyl or halogen.

Preferred halogenocycloalkanes (D) are those of the general formula

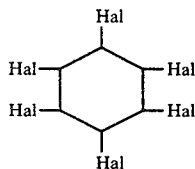

in which Hal denotes halogen (especially chlorine).

Preferred halogenoalkanes (E) are those of the general formula

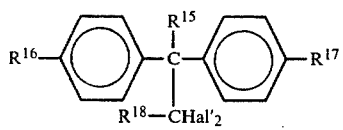

in which
Hal' represents chlorine or bromine,
R$^{15}$ represents hydrogen or hydroxyl,
R$^{16}$ and R$^{17}$, which may be identical or different, each represent halogen, alkyl or alkoxy and
R$^{18}$ represents hydrogen or halogen.

Particularly preferred halogenoalkanes (VI) are those in which
R$^{15}$ denotes hydrogen or hydroxyl,
R$^{16}$ and R$^{17}$ are identical and represent halogen, alkyl with 1 to 4 carbon atoms or alkoxy with 1 to 4 carbon atoms and
R$^{18}$ denotes halogen.

Phosphorus-containing compounds of the formula (I) are known and they are all producible by customary processes. The phosphorus-containing compounds of the general formula (I) which can be used according to the invention include certain phosphoric acid esters, thiophosphoric acid esters, dithiophosphoric and trithiophosphoric acid esters, phosphonic acid esters, thiophosphonic acid esters and dithiophosphonic acid esters and phosphinic acid esters and thiophosphinic acid esters. The preparation of (thio-)phosphoric acid esters, (thio-)phosphonic acid esters or (thio-)phosphinic acid esters is described in detail, for example, in Houben-Weyl, "Methoden der Organischen Chemie" ("Methods of Organic Chemistry"), Volume 12/1 and Volume 12/2.

The phosphonic acid derivatives and phosphinic acid derivatives are preferably prepared from the corresponding phosphorous acid triesters and phosphonous acid diesters and a (meth-)allyl halide by a nickel-catalyzed Arbusow reaction according to the processes described in German Offenlegungsschriften (German Published Specifications) Nos. 2,442,427, 2,442,428 and 2,601,427. Phosphonate esters with different ester radicals, thiophosphonic acid O,S-diesters or phosphonic acid ester-amides are obtainable from the phosphonic acid diesters via the intermediate stage of the phosphonic acid ester-chloride. Phosphonic acid ester-chlorides are easily formed from the diesters by the action of phosphorus pentachloride, phosgene or oxalyl chloride at temperatures of up to about 100° C. (in this context see: Houben-Weyl, "Methoden der Organischen Chemie" ("Methods of Organic Chemistry"), Volume 12/1, page 415 et seq.). The esterchlorides can be reacted with alcohols, phenols, amines, anilines, mercaptans or thiophenols by known processes; see, for example, Houben-Weyl, "Methoden der Organischen Chemie" ("Methods of Organic Chemistry"), Volume 12/1, pages 423 et seq., 529 et seq. and 577 et seq.

Examples of phosphorus-containing compounds of the formula (I) which can particularly advantageously be used as synergistic agents are: allylmethylphosphinic acid methyl ester, allylmethylphosphinic acid ethyl ester, allylmethylphosphinic acid allyl ester, allylmethylphosphinic acid propargyl ester, allylmethylphosphinic acid n-propyl ester, allylmethylphosphinic acid i-propyl ester, allylmethylphosphinic acid n-butyl ester, allylmethylphosphinic acid i-butyl ester, allylmethylphosphinic acid 2-butyl ester, allylmethylphosphinic acid amyl ester, allylmethylphosphinic acid isoamyl ester, allylmethylphosphinic acid n-hexyl ester, allylmethylphosphinic acid 2-ethylhexyl ester, allylmethylphosphinic acid 2,2-dichlorovinyl ester, allylphenylphosphinic acid methyl ester, allylphenylphosphinic acid ethyl ester, allylphenylphosphinic acid allyl ester, allylphenylphosphinic acid propargyl ester, allylphenylphosphinic acid n-propyl ester, allylphenylphosphinic acid i-propyl ester, allylphenylphosphinic acid n-butyl ester, allylphenylphosphinic acid i-butyl ester, allylphenylphosphinic acid 2-butyl ester, allylphenylphosphinic acid amyl ester, allylphenylphosphinic acid isoamyl ester, allylphenylphosphinic acid n-hexyl ester, allylphenylphosphinic acid 2-ethylhexyl ester, allylphenylphosphinic acid 2,2-dichlorovinyl ester, allylethylphosphonic acid ethyl ester, allylethylphosphinic acid propyl ester, allylethylphosphinic acid isopropyl ester, allylethylphosphinic acid butyl ester, allylethylphosphinic acid isobutyl ester, allylethylphosphinic acid 2,2-dichlorovinyl ester, allylethylphosphinic acid methyl ester, allylethylphosphinic acid ethyl ester, allylethylphosphinic acid 2-chloroethyl ester, allylethylphosphinic acid 2-bromoethyl ester, allylethylphosphinic acid allyl ester, allylethylphosphinic acid propargyl ester, allylethylphosphinic acid n-propyl ester, allylethylphosphinic acid i-propyl ester, allylethylphosphinic acid n-butyl ester, allylethylphosphinic acid i- butyl ester, allylethylphosphinic acid 2-butyl ester, allylethylphosphinic acid 2-chloropropyl ester, allylethylphosphinic acid 2-bromoethyl ester, allylphosphonic acid dimethyl ester, allylphosphonic acid diethyl ester, allylphosphonic acid di-n-propyl ester, allylphosphonic acid di-i-propyl ester, allylphosphonic acid di-2-chloroethyl ester, allylphosphonic acid di-2-bromoethyl ester, allylphosphonic acid di-2-chloropropyl ester, allylphosphonic acid di-2-bromopropyl ester, allylphosphonic acid diallyl ester, allylphosphonic acid allyl ethyl ester, allylphosphonic acid allyl propyl ester, allylphosphonic acid dibutyl ester, allylphosphonic acid diisobutyl ester, allylphosphonic acid di-2-butyl ester, allylphosphonic acid diamyl ester, allylphosphonic acid diisoamyl ester, allylphosphonic acid dihexyl ester, allylphosphonic acid di-2-ethylhexyl ester, allylphosphonic acid methyl benzyl ester, allylphosphonic acid ethyl benzyl ester, allylphosphonic acid propyl benzyl ester, allylphosphonic acid dibenzyl ester, allylphosphonic acid diphenyl ester, allylphosphonic acid methyl phenyl ester, allylphosphonic acid ethyl phenyl ester, allylphosphonic acid methyl 4-chlorophenyl ester, allylphosphonic acid methyl 4-methoxyphenyl ester, allylphosphonic acid di-2-chloroethyl ester, allylphosphonic acid di-2-chloropropyl ester, allylphosphonic acid ethyl propyl ester, allylphosphonic acid propyl butyl ester, allylphosphonic acid bis-2,3-dichloropropyl ester, allylphosphonic acid methyl 2,2-dichlorovinyl ester, allylphosphonic acid ethyl 2,2-dichlorovinyl ester, allylphosphonic acid propyl 2,2-dichlorovinyl ester, allylphosphonic acid isopropyl 2,2-dichlorovinyl ester, allylphosphonic acid butyl 2,2-dichlorovinyl ester, allylphosphonic acid isobutyl 2,2-dichlorovinyl ester, allylmonothiophosphonic acid O-ethyl S-methyl ester, allylmonothiophosphonic acid O-propyl S-methyl ester, allylmonothiophosphonic acid O-butyl S-methyl ester, allylmonothiophosphonic acid O-ethyl S-butyl ester, allylmonothiophosphonic acid O-propyl S-butyl ester, allylmonothiophosphonic acid O-butyl S-butyl ester, allylmonothiophosphonic acid O-ethyl O-2,2,-dichlorovinyl ester, allylmonothiophosphonic acid O-propyl O-2,2-dichlorovinyl ester, allylmonothiophosphonic acid O-isopropyl O-2,2-dichlorovinyl ester, allylmonothiophosphonic acid O-butyl O-2,2-dichlorovinyl ester, allylmonothiophosphonic acid O-isobutyl O-2,2-dichlorovinyl ester, allylmonothiophosphonic acid O,O-dimethyl ester, allylmonothiophosphonic acid O,O-diethyl ester, allylmonothiophosphonic acid dichloroethyl ester, allylmonothiophosphonic acid di-n-propyl ester, allylmonothiophosphonic acid di-isopropyl ester, allylmonothiophosphonic acid di-n-butyl ester, allylmonothiophosphonic acid di-2-butyl ester, allylmonothiophosphonic acid O,S-dimethyl ester, allylmonothiophosphonic acid O,S-diethyl ester, allylmonothiophosphonic acid O-ethyl S-2-hydroxyethyl ester, allyldithiophosphonic acid O-ethyl S-methyl ester, methanephosphonic acid diallyl ester, methanephosphonic acid methyl allyl ester, methanephosphonic acid ethyl allyl ester, methanesphosponic acid propyl allyl ester, methanephosphonic acid butyl allyl ester, methanephosphonic acid allyl 2,3-dichloropropyl ester, methanephosphonic acid allyl 2,3-dibromopropyl ester, chloromethanephosphonic acid diallyl ester, chloromethanephosphonic acid methyl allyl ester, chloromethanephosphonic acid ethyl allyl ester, chloromethanephosphonic acid propyl allyl ester, chloromethanephosphonic acid butyl allyl ester, chloromethanephosphonic acid allyl 2,3-dichloropropyl ester, chloromethanephosphonic acid allyl 2,3-dibromopropyl ester, butene-2-phosphonic acid dimethyl ester-1, butene-2-phosphonic acid diethyl ester-1, butene-2-phosphonic acid dipropyl ester-1, triallyl phosphate, tripropargyl phosphate, ethanephosphonic acid diallyl ester, ethanephosphonic acid methyl allyl ester, ethanephosphonic acid ethyl allyl ester, ethanephosphonic acid n-propyl allyl ester, ethanephosphonic acid i-propyl allyl ester, ethanephosphonic acid n-butyl allyl ester, ethanephosphonic acid i-butyl allyl ester, propanephosphonic acid diallyl ester, propanephosphonic acid methyl allyl ester, propanephosphonic acid ethyl allyl ester, propanephosphonic acid n-propyl allyl ester, propanephosphonic acid i-propyl allyl ester, propanephosphonic acid n-butyl allyl ester, propanephosphonic acid i-butyl allyl ester, vinylphosphonic acid diallyl ester, vinylphosphonic acid methyl allyl ester, vinylphosphonic acid ethyl allyl ester, vinylphosphonic acid n-propyl allyl ester, vinylphosphonic acid i-propyl allyl ester, vinylphosphonic acid n-butyl allyl ester, vinylphosphonic acid i-butyl allyl ester, 1-methylvinylphosphonic acid diallyl ester, 1-methylvinylphosphonic acid methyl allyl ester, 1-methylvinylphosphonic acid ethyl allyl ester, 1-methylvinylphosphonic acid n-propyl allyl ester, 1-methylvinylphosphonic acid i-propyl allyl ester, 1-methylvinylphosphonic acid n-butyl allyl ester, 1-methylvinylphosphonic acid i-butyl allyl ester, 2,2-dimethylvinylphosphonic acid diallyl ester, 2,2-dimethylvinylphosphonic acid methyl allyl ester, 2,2-dimethylvinylphosphonic acid ethyl allyl ester, 2,2-dimethylvinylphosphonic acid n-propyl allyl ester, 2,2-dimethylvinylphosphonic acid i-propyl allyl ester, 2,2-dimethylvinylphosphonic acid n-butyl allyl ester, 2,2-dimethylvinylphosphonic acid i-butyl allyl ester, benzylphosphonic acid diallyl ester, benzylphosphonic acid methyl allyl ester, benzylphosphonic acid ethyl allyl ester, benzylphosphonic acid n-propyl allyl ester, benzylphosphonic acid i-propyl allyl ester, benzylphosphonic acid n-butyl allyl ester, benzylphosphonic acid i-butyl allyl ester, 1-phenylvinylphosphonic acid diallyl ester, 1-phenylvinylphosphonic acid methyl allyl ester, 1-phenylvinylphosphonic acid ethyl allyl ester, 1-phenylvinylphosphonic acid n-propyl allyl ester, 1-phenylvinylphosphonic acid i-propyl allyl ester, 1-phenylvinylphosphonic acid n-butyl allyl ester, 1-phenylvinylphosphonic acid i-butyl allyl ester, phenylphosphonic acid diallyl ester, phenylphosphonic acid methyl allyl ester, phenylphosphonic acid ethyl allyl ester, phenylphosphonic acid n-propyl ally ester, phenylphosphonic acid i-propyl allyl ester, phenylphosphonic acid n-butyl allyl ester, phenylphosphonic acid i-butyl allyl ester, phenylthiophosphonic acid diallyl ester, phenylthiophosphonic acid methyl allyl ester, phenylthiophosphonic acid ethyl allyl ester, phenylthiophosphonic acid n-propyl allyl ester, phenylthiophosphonic acid i-propyl allyl ester, phenylthiophosphonic acid n-butyl allyl ester, phenylthiophosphonic acid i-butyl allyl ester, 1-ethoxy vinylphosphonic acid diallyl ester, 1-ethoxy vinylphosphonic acid methyl allyl ester, 1-ethoxyvinylphosphonic acid ethyl allyl ester, 1-ethoxy vinylphosphonic acid n-propyl allyl ester, -ethoxy ylenephosphonic acid i-propyl allyl ester, 1-ethoxy vinylphosphonic acid n-butyl allyl ester, 1-ethoxy vinylphosphonic acid i-butyl allyl ester, phosphoric acid diethyl allyl ester, phosphoric acid dipropyl allyl ester, phosphoric acid diisopropyl allyl ester, phosphoric acid dibutyl allyl ester, phosphoric acid dichloroethyl allyl ester, phosphoric acid dibenzyl allyl ester, phosphoric acid methyl diallyl ester, phosphoric acid ethyl diallyl ester, phosphoric acid propyl diallyl ester, phosphoric acid isopropyl diallyl ester, phosphoric acid butyl diallyl ester, phosphoric acid chloroethyl diallyl ester, phosphoric acid allyl bis-2,3-dichloropropyl ester, phosphoric acid allyl bis-2,3-dibromopropyl ester, phosphoric acid diallyl 2,3-di-chloropropyl ester, phosphoric acid diallyl 2,3-dibromopropyl ester, phosphoric acid allyl methyl 2,2-di-chlorovinyl ester, phosphoric acid allyl ethyl 2,2-dichlorovinyl ester, phosphoric acid allyl propyl 2,2-di-chlorovinyl ester, phosphoric acid allyl isopropyl 2,2-di-chlorovinyl ester, phosphoric acid allyl butyl 2,2-dichlorovinyl ester, phosphoric acid allyl isobutyl 2,2-dichlorovinyl ester, phosphoric acid diallyl 2,2-dichlorovinyl ester, phosphoric acid allyl bis-2,2-dichlorovinyl ester, O,O,O-triallyl thiophosphate, O,O,O-tripropargyl thiophosphate, thiophosphoric acid O-allyl O,O-dimethyl ester, thiophosphoric acid O-allyl O,O-diethyl ester, thiophosphoric acid O-allyl O,O-dipropyl ester, thiophosphoric acid O-allyl O,O-dipropyl ester, thiophosphoric acid O-allyl O,O-diisopropyl ester, thiophosphoric acid O-allyl O,O-dibutyl ester, thiophosphoric acid O-allyl O,O-di-2-chloroethyl ester, thiophosphoric acid O,O-diallyl O-methyl ester, thiophosphoric acid O,O-diallyl O-ethyl ester, thiophosphoric acid O,O-diallyl O-propyl ester, thiophosphoric acid O,O-diallyl O-isopropyl ester, thiophosphoric acid O,O-diallyl dibutyl ester, thiophosphoric acid O,O-diallyl O-di-2-chloroethyl ester, phosphoric acid methyl dipropargyl ester, phosphoric acid ethyl dipropargyl ester, phosphoric acid propyl dipropargyl ester, phosphoric acid isopropyl dipropargyl ester, phosphoric acid butyl dipropargyl ester, phosphoric acid isobutyl dipropargyl ester, phosphoric acid amyl dipropargyl ester, phosphoric acid isoamyl dipropargyl ester, phosphoric acid hexyl dipropargyl ester, phosphoric acid 2-ethylhexyl dipropargyl ester, phosphoric acid diethyl propargyl ester, phosphoric acid diisopropyl propargyl ester, and phosphoric acid di-n-propyl propargyl ester.

The carbamates (group A) of the formula (II) which may be used as components of the mixture include: 2-methylphenyl, 2-ethylphenyl, 2-n-propylphenyl, 2-methoxyphenyl, 2-ethoxyphenyl, 2-n- or -iso-propoxyphenyl, 4-methylphenyl, 4-ethylphenyl, 4-n-propylphenyl, 4-methoxyphenyl, 4-ethoxyphenyl, 4-n-propoxyphenyl, 2-allylphenyl, 2-(1-methylallyl)-phenyl, 3-isopropyl-4-methoxyphenyl, 3,4,5-trimethylphenyl, 2,3-dihydro-2,2-dimethylbenzofuran-7-yl, 2-[1,3-dioxolan-2-yl-phenyl], 2,2-dimethyl-1,3-benzodioxol-4-yl and 2,2-dimethyl and 1-methyl-2,3-dihydro-benzofuran-4-yl N-methyl-carbamate and the corresponding N-methyl-N-acetyl-, N-methyl-N-trifluoromethylthio-, N-methyl-N-dichloromonofluoromethylthio and N-methyl-N-dimethylaminothio-carbamates.

These compounds, their preparation and their use are known (see, for example, U.S. Pat. Nos. 3,009,855; 2,903,478 and 3,111,539).

The carboxylic acid esters (group B) of the formula (III) which may be used as components in the mixture include:

acetic acid 2,2,2-trichloro-1-(3,4-dichlorophenyl)-ethyl ester, 2,3,4,5-tetrahydrophthalimidomethyl chrysanthemate, 3-phenoxybenzyl 2,2-dimethyl-3-(2,2-dichlorovinyl)-cyclopropane-carboxylate and (5-benzyl-furyl)-methyl 2,2-dimethyl-3-(2-methylpropenyl)-cyclopropanecarboxylate.

The compounds listed are known and in many cases are generally known commercial products (see R. Wegler "Chemie der Pflanzenschutz- und Schädlingsbekämpfungsmittel" ("Chemistry of Plant Protection Agents and Agents for Combating Pests") Volume 1, pages 87–118, Heidelberg (1970)).

The phosphoric acid esters (group C) of the formula (IV) which may be used as components in the mixture include: O,O-dimethyl and O,O-diethyl O-(2,2-dichloro-and 2,2-dibromovinyl) phosphoric acid esters or thionophosphoric acid esters and O,O-dimethyl and O,O-diethyl O-(3-methyl-4-methylthiophenyl) phosphoric and thionophosphoric acid esters.

The compounds of the formula (IV) are known and are readily producible by processes known from the literature (see, for example, U.S. Pat. No. 2,956,073, German Auslegeschrift (German Published Specification) No. 1,167,324 and Belgian Pat. No. 633,478).

The cycloalkanes (group D) of the formula (V) which may be used as components in the mixture include: 1,2,3,4,5,6-hexachlorocyclohexane. This compounds, its preparation and its use are known (see, for example U.S. Pat. No. 2,502,258; Chem.+Industry, 1945, page 314).

The halogenoalkanes (group E) of the formula (VI) which may be used as components in the mixture include:

1,1,1-trichloro-2,2-bis-(4-chloro- or 4-methoxyphenyl)-ethane, 1,1,1-trichloro-2,2-bis-(4-chlorophenyl)-2-hydroxy-ethane and 1,1-dichloro-2,2-bis-(4-ethylphenyl)-ethane.

These compounds, their preparation and their use are known (see, for example, U.S. Pat. Nos. 2,420,928, 2,464,600, 2,883,428 and 2,917,553).

The weight ratios of the groups of active compounds can vary within relatively wide ranges. In general, the phosphorus-containing compound (1) is employed with the remaining active compound(s) in a weight ratio of about 0.1:10 to 10:0.1. However, a weight ratio of about 0.5:1 to 3.0:1.0 has proved particularly suitable.

The active compound combinations according to the invention not only produce a rapid knock-down action, but also cause the lasting destruction of arthropod pests, especially of insects and mites, which are encountered in agriculture, in forestry, in the protection of stored products and of materials, and in the hygiene field. They are active against normally sensitive and resistant varieties and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratoriodes, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix*, Pemphigus spp., *Pediculus humanus corporia*, Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aluerodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, macrosiphum avenae, Myzus spp., Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor, Agriotes spp., Conoderus spp., Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypoobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylene or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general certain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 99% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides a method of combating arthropods, especially insects or acarids, which comprises applying to the arthropods, or to a habitat thereof, a composition according to the present invention.

The present invention also provides crops protected from damage by arthropods by being grown in areas in which immediately prior to and/or during the time of the growing a composition according to the present invention was applied.

The following table identifes synergistic agents by name and number and indicates the example hereinbelow where they are synthesized:

TABLE 1

| Synergistic Agent No. | Name | Example |
|---|---|---|
| 1 | Allylphosphonic acid propyl allyl ester | 6 |
| 2 | Chloromethanephosphonic acid diallyl ester | 7 |
| 3 | Allyl diethyl phosphate | 15 |
| 4 | Allyl dipropyl phosphate | 15 |
| 5 | Allyl di-n-butyl phosphate | 15 |
| 6 | Propanephosphonic acid ethyl allyl ester | 4 |
| 7 | Allyl diphenyl phosphate | 13 |
| 8 | Allylphosphonic acid dimethyl ester | 2 |
| 9 | Allylphosphonic acid diethyl ester | 2 |
| 10 | Allylphosphonic acid di-n-propyl ester | 2 |
| 11 | Allylphosphonic acid diisopropyl ester | 2 |
| 12 | Allylphosphonic acid di-n-butyl ester | 2 |
| 13 | Allylphosphonic acid diisobutyl ester | 2 |
| 14 | Allylphosphonic acid diallyl ester | 2 |
| 15 | Allylphosphonic acid bis-2-chloroethyl ester | 2 |
| 16 | Allylmethylphosphinic acid ethyl ester | 1 |
| 17 | Allylmethylphosphinic acid isopropyl ester | 1 |
| 18 | Allylmethylphosphinic acid butyl ester | 1 |

TABLE 1-continued

| Synergistic Agent No. | Name | Example |
|---|---|---|
| 19 | Allylethylphosphinic acid ethyl ester | 1 |
| 20 | Allylphenylphosphinic acid ethyl ester | 1 |
| 21 | Cis/trans-2-butene-1-phosphonic acid diethyl ester | 2 |
| 22 | Propargyl diethyl phosphate | 15 |
| 23 | Propyl dipropargylphosphate | 16 |
| 24 | Allylthiophosphonic acid O,O-di-ethyl ester | 3 |
| 25 | Allylphosphonic acid ethyl allyl ester | 2 |
| 26 | Allylphosphonic acid ethyl phenyl ester | 5 |
| 27 | Triallyl phosphate | 14 |
| 28 | Isobutyl dipropargyl phosphate | 16 |
| 29 | Isopropyl dipropargyl phosphate | 16 |
| 30 | Propargyl dipropyl phosphate | 15 |
| 31 | Propargyl dibutyl phosphate | 15 |
| 32 | Methanephosphonic acid diallyl ester | 8 |
| 33 | Phosphoric acid ethyl bis-propargyl ester | 9 |
| 34 | Phosphoric acid allyl dimethyl ester | 10 |
| 35 | Phosphoric acid propargyl dimethyl ester | 11 |
| 36 | 1-Methoxyvinylphosphonic acid diethyl ester | 12 |
| 37 | 2-Methylallylmethylphosphinic acid ethyl ester | 1 |

Preparation of the compounds having a synergistic action is carried out as follows:

EXAMPLE

General instructions for the preparation of alkyl phosphinates.

1 mole of the relevant phosponus acid alkyl ester was initially introduced into a reaction vessel together with 4 g of Raney nickel, $NiCl_2$, $NiBr_2$ or $\pi$-allyl-nickel chloride, under a $N_2$ atmosphere, and the mixture was heated to 80° to 120° C. 1.1 moles of allyl chloride or bromine were slowly added dropwise at this temperature and the alkyl halide liberated was distilled off.

After adding 0.5 g of phenothiazine, the reaction mixture was carefully fractionated.

The allylphosphinates (and also the allylphosphonates) tended to isomerize to the 1-propene-1-phosphinate (or -phosphonate) at high temperatures. A reaction temperature of 130° C. should therefore not be exceeded.

The presence of 1-propene-1-phosphinates (or -phosphonates) could be detected very rapidly by NMR spectroscopy. Allylethylphosphinic acid ethyl ester which was known to have isomerized exhibited, in the NMR spectrum, the newly occurring vinyl proton

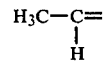

at 6.78 ppm (d,d,q), $J_{PH}=13$ Hz, $J_{H,H\ trans}=17$ Hz and $J_{H,CH_3}=7$ Hz. The pure allylphosphinate ester exhibited no resonance at all at >6.3 ppm. All the allylphosphinates and allylphosphonates mentioned below were isomer-free.

The following table shows compounds which were obtainable by the process indicated above.

TABLE 2:

| Synergistic Agent No. | Synergistic Agent | Boiling point | $n_D^{20}$ |
|---|---|---|---|
| 16 | Allylmethylphosphinic acid ethyl ester | 100° C./16 mm Hg | 1.4492 |
| 17 | Allylmethylphosphinic acid isopropyl ester | 95-97° C./11 mm Hg | 1.4448 |
| 18 | Allylmethylphosphinic acid butyl ester | 123-5° C./14 mm Hg | 1.4475 |
| 19 | Allylethylphosphinic acid ethyl ester | 106-7° C./14 mm Hg | 1.4503 |
| 20 | Allylphenylphosphinic acid ethyl ester | 102° C./0.1 mm Hg | 1.5218 |

TABLE 2:-continued

| Synergistic Agent No. | Synergistic Agent | Boiling point | $n_D^{20}$ |
|---|---|---|---|
| 37 | 2-Methylallylmethylphosphinic acid ethyl ester | 102-7° C./13 mm Hg | 1.452 |

EXAMPLE 2

General instructions for the preparation of allyl-phosphonates.

1 mole of the relevant trialkyl phosphite was initially introduced, together with 4 g of Raney nickel, nickel tetracarbonyl, π-allyl-nickel chloride or nickel chloride, under a nitrogen atmosphere. Allyl chloride or bromide was added dropwise at 80° to 120° C. and the alkyl halide formed was distilled off. After adding 1 g of phenothiazine, the reaction mixture was fractionated in vacuo.

The following table shows compounds which were obtainable by the process indicated above:

TABLE 3

| Synergistic Agent No. | Synergistic Agent | Boiling point | $n_D^{20}$ |
|---|---|---|---|
| 8 | Allylphosphonic acid dimethyl ester | 90-92° C./14 mm Hg | 1.4397 |
| 9 | Allylphosphonic acid diethyl ester | 93-96° C./10 mm Hg | 1.4330 |
| 10 | Allylphosphonic acid di-n-propyl ester | 122-23° C./13 mm Hg | 1.4352 |
| 11 | Allylphosphonic acid diisopropyl ester | 102° C./14 mm Hg | 1.4265 |
| 12 | Allylphosphonic acid di-n-butyl ester | 140-1° C./12 mm Hg | 1.4385 |
| 13 | Allylphosphonic acid diisobutyl ester | 128-9° C./11 mm Hg | 1.4348 |
| 14 | Allylphosphonic acid diallyl ester | 69-71° C./0.3 mm Hg | 1.4730 |
| 15 | Allylphosphonic acid bis-2-chloroethyl ester | 124° C./0.25 mm Hg | 1.4788 |
| 21 | Cis/trans-2-butene-1-phosphonic acid diethyl ester | 111° C./12 mm Hg | 1.4390 |
| 25 | Allylphosphonic acid ethyl allyl ester | 63° C./0.08 mm Hg | 1.4485 |

EXAMPLE 3

Allylthiophosphonic acid O,O-di-ethyl ester 1 mole of thiophosphorous acid O,O-diethyl ester was dissolved in 600 ml of absolute benzene, and 1 mole of sodium ethylate, dissolved in absolute ethanol, was added at 0°-5° C., while cooling. 1.15 moles of allyl bromide were added dropwise to this mixture at 0°-5° C. and the mixture was stirred at 10° to 20° C. for a further 2 hours and at 40° C. for 3 hours. The NaBr which had separated out was filtered off and the filtrate was distilled.

Yield: 60 g.
Boiling point: 53°-54° C./0.3 mm Hg.
$n_D^{20}$: 1.4738.

EXAMPLE 4

Propanephosphonic acid ethyl allyl ester 200 g of phosgene were passed into 1 mole of propane-phosphonic acid diethyl ester at 70°-80° C. The mixture was stirred at 70°-80° C. for 1 hour and a dry N₂ stream was passed through the reaction mixture overnight at 50° C. The mixture was completely degassed at 50° C. under a waterpump vacuum in a Rotavapor and crude propanephosphonic acid ethyl ester-chloride was obtained. This was rendered basic with absolute pyridine, dissolved in 300 ml of toluene and reacted with a mixture of 1.1 moles of pyridine and 1 mole of allyl alcohol at 20°-30° C. The mixture was allowed to after-react at 80° C. for 2 hours. The solution which was separated off from the hydrochloride by filtration was concentrated and distilled.

Yield: 124 g (60%).
Boiling point: 107.5°-108.5° C./11 mm Hg.
$n_D^{20}$: 1.4348.

EXAMPLE 5

Allylphosphonic acid ethyl phenyl ester

Allylphosphonic acid ethyl ester-chloride, prepared analogously to synergistic agent 16, was reacted with phenol analogously to agent 16 to give allylphosphonic acid ethyl phenyl ester.

Yield: 60%.
Boiling point: 96°-98° C./0.07.
$n_D^{20}$: 1.5036.

EXAMPLE 6

Allylphosphonic acid propyl allyl ester

The product from allylphosphonic acid dipropyl ester and allyl alcohol was prepared analogously to synergistic agent 6.

Boiling point: 83° C./0.1 mm Hg.
$n_D^{20}$: 1.4460.

EXAMPLE 7

Chloromethanephosphonic acid diallyl ester

This was prepared by reacting 1 mole of chloromethane-phosphonic acid dichloride with 2 moles of allyl alcohol in the presence of excess pyridine in toluene.

Boiling point: 100° C./0.18 mm Hg.
$n_D^{20}$: 1.4682.

EXAMPLE 8

Methanephosphonic acid diallyl ester

This was prepared analogously to synergistic agent 2 from methanephosphonic acid dichloride and allyl alcohol.

Boiling point 56°-60° C./0.07-0.13 mm Hg.
$n_D^{20}$: 1.4475.

EXAMPLE 9

Phosphoric acid ethyl bis-propargyl ester 1 mole of phosphoric acid ethyl ester-dichloride and 2 g of phenothiazine were dissolved in 350 ml of toluene, and a mixture of 2.4 moles of pyridine and 2 moles of propargyl alcohol was added at 10°-20° C. The reaction mixture was subsequently stirred at 20°-30° C. for 1 hour and at 60° C. for 1 hour and the hydrochloride which had separated out was filtered off. The salt was dissolved in a little water and the solution was extracted twice with 100 ml of methylene chloride.

The toluene was stripped off from the two-phase filtrate, the residue was dissolved in 500 ml of methylene chloride, and the methylene chloride phase from the salt extraction was added. This solution was washed several times with saturated sodium bicarbonate solution and water and was dried with sodium sulphate. The methylene chloride was stripped off and the residue was fractionated.

Boiling point: 99° C./0.03 mm Hg.
$n_D^{20}$: 1.4488.

EXAMPLE 10

Phosphoric acid allyl dimethyl ester 1 mole of phosphoric acid dimethyl ester-chloride was reacted with 1 mole of allyl alcohol analogously to Example 9.

Boiling point: 73° C./2 mm Hg.
$n_D^{20}$: 1.4250.

EXAMPLE 11

Phosphoric acid propargyl dimethyl ester 1 mole of phosphoric acid dimethyl ester-chloride was reacted with 1 mole of propargyl alcohol analogously to Example 9.

Boiling point: 71°-72° C./0.22 mm Hg.
$n_D^{20}$: 1.4282.

EXAMPLE 12

1-Methoxyvinylphosphonic acid diethyl ester 0.9 mole of methyl 1,2-dichloroethyl ether was added dropwise to 1 mole of triethyl phosphite at 120° C., under a $N_2$ atmosphere. After a reaction time of 8 hours, the mixture was fractionated. 120 g of 1-methoxy-2-chloroethane-phosphonic acid diethyl ester were obtained.

Boiling point: 77°-79° C./0.1 mm Hg.
$n_D^{20}$: 1.4427.

1 mole of this compound was dissolved in 100 ml of alcohol. A solution of 1 mole of KOH in 200 ml of alcohol was slowly added at 20°-30° C. and the temperature was kept below 40° C. by cooling. The mixture was filtered and, after adding 0.5 g of phenothiazine, the filtrate was fractionated.

Yield: 140 g.
Boiling point: 85° C./0.5 mm Hg.
$n_D^{20}$: 1.4412.

EXAMPLE 13

Allyl diphenyl phosphate

This was prepared from allyl alcohol and phosphoric acid diphenyl ester-chloride in the presence of pyridine.

Boiling point: 148°-150° C./0.15 mm Hg.
$n_D^{20}$: 1.5348.

EXAMPLE 14

Triallyl phosphate

This was prepared from $POCl_3$ and allyl alcohol in toluene/triethylamine

Boiling point: 90° C./0.15 mm Hg.
$n_D^{20}$: 1.4482.

EXAMPLE 15

General instructions for the preparation of allyl dialkyl phosphates and propargyl dialkyl phosphates 1.2 moles of triethylamine were added dropwise to 1 mole of dialkyl phosphite, 2 moles of $CCl_4$ and 1.05 moles of allyl alcohol or propargyl alcohol at 20°-30° C. After the exothermic reaction had subsided, the mixture was refluxed for 3 hours, the salt was filtered off and the filtrate was fractionated.

The following table shows compounds which were obtainable by the process indicated above (Table 4):

EXAMPLE 16

General instructions for the preparation of alkyl dipropargyl phosphates.

1.5 moles of $POCl_3$ were mixed under cooling with 5 moles of triethylamine. At $-20°$ C. 1.5 moles of the corresponding alkanol were added dropwise. After the exothermic reaction had subsided, 3 moles of propargylic alcohol were added dropwise. 800 ml of methylenechloride were added, the mixture was stirred for 1 hour at room temperature. The hydrochloride was filtered, the filtrate was washed with diluted $NaCO_3$-solution and destilled in vacuo. The following Table 5 shows compounds which were obtainable by this process:

TABLE 4

| Synergistic Agent No. | Synergistic Agent | Boiling point | $n_D^{20}$ |
|---|---|---|---|
| 3 | Allyl diethyl phosphate | 68° C./0.45 mm Hg | 1.4216 |
| 4 | Allyl dipropyl phosphate | 75° C./0.2 mm Hg | 1.4265 |
| 5 | Allyl di-n-butyl phosphate | 102° C./0.06 mm Hg | 1.4295 |
| 22 | Propargyl diethyl phosphate | 80° C./0.3 mm Hg | 1.4320 |
| 30 | Propargyl dipropyl phosphate | 94° C./0.15 mm Hg | 1.4332 |
| 31 | Propargyl dibutyl phosphate | 111° C./0.03 mm Hg | 1.4364 |

TABLE 5

| Synergistic Agent No. | synergistic Agent | Boiling point | $n_D^{20}$ |
|---|---|---|---|
| 23 | Propyl dipropargyl phosphate | 106° C./0.2 mm Hg | 1,4512 |
| 28 | Isobutyl dipropargyl phosphate | 100° C./0.1 mm Hg | 1,4475 |
| 29 | Isopropyl dipropargyl phosphate | 98 C./0.1 mm Hg | 1,4475 |

The arthropodicidal activity of the compositions of this invention is illustrated by the following examples:

EXAMPLE 17

$LT_{100}$ test

Test insects: *Musca domestica* (Weymands strain), resistant to phosphoric acid esters Solvent: Acetone Solutions were prepared from the active compounds, synergistic agents and mixtures of active compounds and synergistic agents, and 2.5 ml of each solution were pipetted onto a respective filter paper disc of 9.5 cm diameter in a Petri dish. The filter paper absorbed the solution. The Petri dish was left standing open until the solvent had completely evaporated. 25 test insects were then introduced into each Petri dish, and the dish was covered with a glass lid.

The condition of the test insects was checked continuously for up to 6 hours. The time required for a 100% knock-down action was determined. If the $LT_{100}$ was not reached after 6 hours, the percentage of the test insects which had been knocked down was determined.

The concentrations of the active compounds, synergistic agents and mixtures, and their actions, can be seen from the table which follows.

TABLE 6

LT 100 Test with *Musca domestica* (Weymanns strain), resistant to phosphoric acid esters

| Active compounds and ( ) identifying letter | Synergistic agents ( ) No. | Concentration in % | LT 100 after minutes |
|---|---|---|---|
| (A) o-isopropoxyphenyl N-methylcarbamate | | 1.0 | 360' = 0% |
| (B) 2,2-dimethyl-2,3-dihydrobenzofuran-7-yl N-methylcarbamate | | 1.0 | 360' = 20% |
| (C) 1,1-dimethylindan-4-yl N-methylcarbamate | | 1.0 | 360' = 0% |
| (D) o-(ethylthiomethyl)phenyl N-methylcarbamate | | 1.0 | 360' = 0% |
| (E) 2,2-dimethyl-1,3-benzodioxol-4-yl N-methylcarbamate | | 1.0 | 360' = 10% |
| (F) o-(1,3-dioxolan-2-yl)phenyl N-methylcarbamate | | 1.0 | 360' = 10% |
| (G) 4-isopropyl-3-methoxyphenyl N-methylcarbamate | | 1.0 | 360' = 0% |
| (H) methomyl: $CH_3-NH-C(=O)-O-N=C(CH_3)-S-CH_3$ | | 0.04 | 360' = 10% |
| (I) 2-methylindan-4-yl N-methylcarbamate | | 1.0 | 360' = 0% |
| Pyrethrins as a 25% strength extract | | 0.04 | 360' = 15% |

TABLE 6-continued
LT 100 Test with *Musca domestica* (Weymanns strain), resistant to phosphoric acid esters

| Compound | Dose | Time/Effect |
|---|---|---|
| (K) 4-F-C₆H₄-O-C₆H₄-CH(CN)-O-CO-CH(CH(CH₃)₂)-C₆H₄-Cl | 0.2 | 105′ |
| (L) (CH₃)₂C=CH-cyclopropyl(CH₃)₂-C(O)-CH₂-N(tetrahydroisoquinoline-1,3-dione) | 0.04 | 360′ = 90% |
| (M) Cl₂C=CH-cyclopropyl(CH₃)₂-C(O)-O-CH₂-C₆H₄-O-C₆H₅ | 0.2 | 120′ |
| (N) (CH₃)₂C=CH-cyclopropyl(CH₃)₂-C(O)-O-CH₂-furyl-CH₂-C₆H₅ | 0.04 | 360′ = 60% |
| (O) 3,4-Cl₂-C₆H₃-CH(CCl₃)-O-C(O)-CH₃ | 1.0 | 360′ = 70% |
| (P) C₆H₆Cl₆ (hexachlorocyclohexane) | 1.0 | 240′ |
| (Q) (4-Cl-C₆H₄)₂CH-CCl₃ | 1.0 | 360′ = 75% |
| (R) (4-CH₃O-C₆H₄)₂CH-CCl₃ | 1.0 | 360′ = 50% |
| (S) 3-Cl-4-CH₃-coumarin-7-yl-O-P(S)(OC₂H₅)₂ | 1.0 | 360′ = 90% |
| (T) CCl₂=CH-O-P(O)(OCH₃)₂ | 0.008 | 360′ = 90% |
| (U) CH₃NH-C(O)-CH₂-S-P(O)(OCH₃)₂ | 1.0 | 360′ = 95% |
| (V) benzotriazin-CH₂-S-P(S)(OCH₃)₂ | 1.0 | 360′ = 95% |
| (W) | | |

TABLE 6-continued

LT 100 Test with *Musca domestica* (Weymanns strain), resistant to phosphoric acid esters

| Structure | Concentration in % | LT 100 after minutes |
|---|---|---|
| $CCl_3-CH(OH)-P(=O)(OCH_3)_2$    (X) | 1.0 | 360' = 90% |
| $CH_3-S-C_6H_3(CH_3)-O-P(=S)(OCH_3)_2$    (Y) | 1.0 | 360' = 95% |
| $C_2H_5-O-C(=O)-CH(S-P(=S)(OCH_3)_2)-CH_2-C(=O)-O-C_2H_5$    (Z) | 1.0 | 360' = 15% |

| Active Compounds and ( ) identifying letter | Synergistic agents ( ) No. | Concentration in % | LT 100 after minutes |
|---|---|---|---|
| | 2,3-dihydro-1,4-benzodioxin-6-yl-$CH_2-OCH_2-CH_2-O-CH_2-CH_2-OC_4H_9$ with $CH_2CH_2-CH_3$ substituent (Piperonyl butoxide) | 1.0 | 360' = 0% |
| | $H_2C=CH-CH_2-P(=O)(OCH_2-CH_2-CH_3)(O-CH_3-CH=CH_2)$    (1) | 0.2 | 360' = 10% |
| | $ClCH_2-P(=O)(OCH_2-CH=CH_2)_2$    (2) | 0.2 | 360' = 0% |
| | $H_2C=CH-CH_2-O-P(=O)(OC_2H_5)_2$    (3) | 1.0 | 360' = 40% |
| | $H_2C=CH-CH_2-O-P(=O)(OC_3H_7)_2$    (4) | 0.2 | 360' = 60% |
| | $H_2C=CH-CH_2O-P(=O)(OC_4H_9)_2$    (5) | 1.0 | 360' = 0% |
| | $H_2C=CH-CH_2-O-P(=O)(OC_2H_5)(CH_2-CH_2-CH_3)$    (6) | 1.0 | 360' = 0% |
| | $H_2C=CH-CH_2O-P(=O)(O-C_6H_5)_2$    (7) | 1.0 | 360' = 0% |
| | $H_2C=CH-CH_2-P(=O)(OCH_3)_2$    (8) | 1.0 | 360' = 0% |
| | $H_2C=CH-CH_2-P(=O)(OC_2H_5)_2$    (9) | 1.0 | 360' = 0% |
| | $H_2C-CH=CH_2-P(=O)(OCH_2-CH_2-CH_3)_2$    (10) | 0.2 | 360' = 60% |

TABLE 6-continued

LT 100 Test with *Musca domestica* (Weymanns strain), resistant to phosphoric acid esters

| Compound | Dose | Time/Mortality |
|---|---|---|
| (11) H₂C=CH—CH₂—P(=O)—[OCH(CH₃)₂]₂ | 1.0 | 360' = 0% |
| (12) H₂C=CH—CH₂—P(=O)(OC₄H₉)₂ | 0.2 | 360' = 5% |
| (13) H₂C=CH—CH₂—P(=O)(OCH₂—CH(CH₃)₂)₂ | 0.2 | 360' = 70% |
| (14) H₂C=CH—CH₂—P(=O)(OCH₂—CH=CH₂)₂ | 1.0 | 360' = 0% |
| (15) H₂C=CH—CH₂—P(=O)—(OCH₂—CH₂Cl)₂ | 1.0 | 360' = 0% |
| (16) H₂C=CH—CH₂—P(=O)(CH₃)(OC₂H₅) | 1.0 | 360' = 0% |
| (17) H₂C=CH—CH₂—P(=O)(CH₃)(OCH(CH₃)₂) | 0.2 | 360' = 0% |
| (18) H₂C=CH—CH₂—P(=O)(CH₃)(OC₄H₉) | 1.0 | 360' = 0% |
| (19) H₂C=CH—CH₂—P(=O)(CH₂—CH₃)(OC₂H₅) | 1.0 | 240' |
| (20) H₂C=CH—CH₂—P(=O)(C₆H₅)(OC₂H₅) | 1.0 | 360' = 0% |
| (21) H₃C—CH=CH—CH₂—P(=O)(OC₂H₅)₂ | 1.0 | 360' = 0% |
| (22) HC≡C—CH₂—O—P(=O)(OC₂H₅)₂ | 1.0 | 360' = 45% |
| (23) H₃C—CH₂—CH₂—O—P(=O)(OCH₂—C≡CH)₂ | 1.0 | 360' = 0% |
| (24) H₂C=CH—CH₂—P(=S)(OC₂H₅)₂ | 1.0 | 360' = 0% |

TABLE 6-continued

LT 100 Test with *Musca domestica* (Weymanns strain), resistant to phosphoric acid esters

| Compound | Conc. | Result |
|---|---|---|
| (25) $H_2C=CH-CH_2-\overset{O}{\underset{\underset{OCH_2-CH=CH_2}{\diagdown}}{\overset{\diagup OC_2H_5}{\overset{\parallel}{P}}}}$ | 1.0 | 360' = 0% |
| (26) $H_2C=CH-CH_2-\overset{O}{\underset{\underset{O-\bigcirc}{\diagdown}}{\overset{\diagup OC_2H_5}{\overset{\parallel}{P}}}}$ | 1.0 | 360' = 75% |
| (27) $\overset{O}{\underset{\parallel}{P}}-(OCH_2-CH=CH_2)_3$ | 1.0 | 360' = 0% |
| (28) $H_3C-\underset{\underset{CH_3}{\mid}}{CH}-CH_2O-\overset{O}{\overset{\parallel}{P}}-(OCH_2-C≡CH)_2$ | 1.0 | 360' = 0% |
| (29) $H_2C=CH-CH_2-\overset{O}{\underset{\underset{OCH_2-C≡CH}{\diagdown}}{\overset{\diagup OC_3H_7}{\overset{\parallel}{P}}}}$ | 0.2 | 360' = 10% |
| (30) $HC≡C-CH_2-O-\overset{O}{\overset{\parallel}{P}}(OC_3H_7)_2$ | 0.2 | 360' = 50% |
| (31) $HC≡C-CH_2-O-\overset{O}{\overset{\parallel}{P}}(OC_4H_9)_2$ | 1.0 | 360' = 5% |
| (32) $H_3C-\overset{O}{\overset{\parallel}{P}}(OCH_2-CH=CH_2)_2$ | 0.2 | 360' = 0% |
| (33) $H_5C_2-O-\overset{O}{\overset{\parallel}{P}}(OCH_2-C≡CH)_2$ | 1.0 | 360' = 55% |
| (34) $H_2C=CH-CH_2-\overset{O}{\overset{\parallel}{P}}(OCH_3)_2$ | 1.0 | 360' = 0% |
| (35) $HC≡C-CH_2-\overset{O}{\overset{\parallel}{P}}(OCH_3)_2$ | 1.0 | 360' = 0% |

| Identifying letter of the active compound | + | Synergistic Agent No. | Concentration of active compound in % | + | Concentration of synergistic agent in % | LT 100 after minutes |
|---|---|---|---|---|---|---|
| A | + | Piperonyl butoxide | 1.0 | + | 1.0 | 180' |
| A | + | 1 | 0.04 | + | 0.04 | 105' |
| A | + | 2 | 0.2 | + | 0.2 | 90' |
| A | + | 3 | 0.2 | + | 0.2 | 105' |
| A | + | 4 | 0.2 | + | 0.2 | 90' |
| A | + | 5 | 0.2 | + | 0.2 | 180' |
| A | + | 6 | 0.2 | + | 0.2 | 90' |
| A | + | 8 | 0.2 | + | 0.2 | 105' |
| A | + | 10 | 0.04 | + | 0.04 | 75' |
| A | + | 10 | 0.008 | + | 0.008 | 360' = 95% |
| A | + | 10 | 0.008 | + | 0.016 | 360' |
| A | + | 10 | 0.008 | + | 0.04 | 180' |
| A | + | 11 | 0.2 | + | 0.2 | 75' |

TABLE 6-continued
LT 100 Test with *Musca domestica* (Weymanns strain), resistant to phosphoric acid esters

| | | | | | | |
|---|---|---|---|---|---|---|
| A | + | 12 | 0.2 | + | 0.2 | 90' |
| A | + | 13 | 0.2 | + | 0.2 | 90' |
| A | + | 14 | 0.2 | + | 0.2 | 75' |
| A | + | 15 | 0.2 | + | 0.2 | 120' |
| A | + | 16 | 1.0 | + | 1.0 | 120' |
| A | + | 17 | 0.04 | + | 0.04 | 75' |
| A | + | 18 | 0.2 | + | 0.2 | 120' |
| A | + | 19 | 0.04 | + | 0.04 | 120' |
| A | + | 20 | 0.2 | + | 0.2 | 105' |
| A | + | 21 | 0.2 | + | 0.2 | 150' |
| A | + | 22 | 0.04 | + | 0.04 | 90' |
| A | + | 22 | 0.008 | + | 0.008 | 150' |
| A | + | 22 | 0.008 | + | 0.016 | 120' |
| A | + | 22 | 0.008 | + | 0.04 | 90' |
| A | + | 23 | 0.008 | + | 0.008 | 360' |
| A | + | 24 | 0.2 | + | 0.2 | 150' |
| A | + | 25 | 0.2 | + | 0.2 | 120' |
| A | + | 26 | 0.04 | + | 0.04 | 150' |
| A | + | 27 | 1.0 | + | 1.0 | 75' |
| A | + | 28 | 0.04 | + | 0.04 | 90' |
| A | + | 29 | 0.04 | + | 0.04 | 75' |
| A | + | 30 | 0.04 | + | 0.04 | 75' |
| A | + | 31 | 1.0 | + | 1.0 | 120' |
| A | + | 32 | 0.04 | + | 0.04 | 150' |
| A | + | 33 | 0.008 | + | 0.008 | 120' |
| A | + | 34 | 0.2 | + | 0.2 | 90' |
| A | + | 35 | 0.008 | + | 0.008 | 120' |
| B | + | Piperonyl butoxide | 0.2 | + | 0.2 | 360' |
| B | + | 1 | 0.04 | + | 0.04 | 120' |
| B | + | 2 | 0.2 | + | 0.2 | 120' |
| B | + | 3 | 0.04 | + | 0.04 | 180' |
| B | + | 8 | 0.04 | + | 0.04 | 120' |
| B | + | 9 | 0.04 | + | 0.04 | 150' |
| B | + | 10 | 0.04 | + | 0.04 | 90' |
| B | + | 11 | 0.04 | + | 0.04 | 120' |
| B | + | 14 | 0.04 | + | 0.04 | 105' |
| B | + | 16 | 0.2 | + | 0.2 | 210' |
| B | + | 32 | 0.04 | + | 0.04 | 90' |
| B | + | 33 | 0.008 | + | 0.008 | 105' |
| B | + | 34 | 0.04 | + | 0.04 | 150' |
| B | + | 35 | 0.008 | + | 0.008 | 150' |
| B | + | 18 | 0.04 | + | 0.04 | 120' |
| B | + | 19 | 0.04 | + | 0.04 | 105' |
| B | + | 20 | 0.2 | + | 0.2 | 210' |
| B | + | 24 | 0.04 | + | 0.04 | 150' |
| B | + | 29 | 0.008 | + | 0.008 | 360' |
| B | + | 30 | 0.04 | + | 0.04 | 75' |
| B | + | 31 | 0.2 | + | 0.2 | 210' |
| B | + | 33 | 0.008 | + | 0.008 | 105' |
| C | + | Piperonyl butoxide | 1.0 | + | 1.0 | 360' = 20% |
| C | + | 3 | 1.0 | + | 1.0 | 360' |
| C | + | 10 | 1.0 | + | 1.0 | 180' |
| C | + | 11 | 1.0 | + | 1.0 | 360' = 95% |
| C | + | 14 | 1.0 | + | 1.0 | 360' = 95% |
| C | + | 18 | 1.0 | + | 1.0 | 240' |
| D | + | Piperonyl butoxide | 1.0 | + | 1.0 | 360' = 90% |
| D | + | 8 | 1.0 | + | 1.0 | 210' |
| D | + | 11 | 1.0 | + | 1.0 | 180' |
| D | + | 14 | 1.0 | + | 1.0 | 150' |
| D | + | 18 | 1.0 | + | 1.0 | 150' |
| D | + | 19 | 1.0 | + | 1.0 | 150' |
| D | + | 24 | 1.0 | + | 1.0 | 180' |
| E | + | Piperonyl butoxide | 0.2 | + | 0.2 | 360' = 40% |
| E | + | 3 | 0.04 | + | 0.04 | 360' = 90% |
| E | + | 8 | 0.2 | + | 0.2 | 150' |
| E | + | 10 | 0.04 | + | 0.04 | 150' |
| E | + | 11 | 0.2 | + | 0.2 | 120' |
| E | + | 14 | 0.04 | + | 0.04 | 360' = 85% |
| E | + | 18 | 0.04 | + | 0.04 | 360' = 80' |
| E | + | 19 | 0.2 | + | 0.2 | 120' |
| E | + | 24 | 0.04 | + | 0.04 | 240' |
| F | + | Piperonyl butoxide | 1.0 | + | 1.0 | 360' = 85% |
| F | + | 3 | 0.2 | + | 0.2 | 180' |
| F | + | 8 | 0.2 | + | 0.2 | 210' |
| F | + | 10 | 0.2 | + | 0.2 | 150' |
| F | + | 11 | 0.2 | + | 0.2 | 210' |
| F | + | 14 | 0.2 | + | 0.2 | 150' |
| F | + | 18 | 0.2 | + | 0.2 | 240' |

TABLE 6-continued

LT 100 Test with *Musca domestica* (Weymanns strain), resistant to phosphoric acid esters

| | | | | | | |
|---|---|---|---|---|---|---|
| F | + | 19 | 0.2 | + | 0.2 | 105' |
| F | + | 24 | 0.2 | + | 0.2 | 360' |
| G | + | Piperonyl butoxide | 1.0 | + | 1.0 | 360' = 30% |
| G | + | 3 | 1.0 | + | 1.0 | 150' |
| G | + | 10 | 0.2 | + | 0.2 | 120' |
| H | + | Piperonyl butoxide | 0.04 | + | 0.04 | 360' = 10% |
| H | + | 8 | 0.04 | + | 0.04 | 360' |
| H | + | 9 | 0.04 | + | 0.04 | 105' |
| H | + | 10 | 0.04 | + | 0.04 | 210' |
| H | + | 11 | 0.04 | + | 0.04 | 360' = 95% |
| H | + | 16 | 0.04 | + | 0.04 | 210' |
| H | + | 19 | 0.04 | + | 0.04 | 360' = 90% |
| I | + | Piperonyl butoxide | 0.2 | + | 0.2 | 360' = 40% |
| I | + | 9 | 0.2 | + | 0.2 | 180' |
| I | + | 16 | 0.2 | + | 0.2 | 240' |
| I | + | 20 | 0.2 | + | 0.2 | 240' |
| K | + | Piperonyl butoxide | 0.04 | + | 0.04 | 180' |
| K | + | 8 | 0.04 | + | 0.04 | 105' |
| K | + | 10 | 0.04 | + | 0.04 | 75' |
| K | + | 18 | 0.04 | + | 0.04 | 120' |
| K | + | 19 | 0.04 | + | 0.04 | 105' |
| L | + | Piperonyl butoxide | 0.04 | + | 0.04 | 105' |
| L | + | 11 | 0.04 | + | 0.04 | 75' |
| L | + | 14 | 0.04 | + | 0.04 | 90' |
| L | + | 18 | 0.04 | + | 0.04 | 90' |
| L | + | 19 | 0.04 | + | 0.04 | 90' |
| M | + | Piperonyl butoxide | 0.04 | + | 0.04 | 120' |
| M | + | 3 | 0.04 | + | 0.04 | 75' |
| M | + | 19 | 0.04 | + | 0.04 | 60' |
| N | + | Piperonyl butoxide | 0.2 | + | 0.2 | 60' |
| N | + | 10 | 0.2 | + | 0.2 | 45' |
| N | + | 11 | 0.2 | + | 0.2 | 45' |
| N | + | 18 | 0.2 | + | 0.2 | 45' |
| N | + | 19 | 0.2 | + | 0.2 | 45' |
| O | + | 9 | 0.04 | + | 0.04 | 120' |
| O | + | 20 | 0.04 | + | 0.04 | 120' |
| P | + | Piperonyl butoxide | 1.0 | + | 1.0 | 360' = 75% |
| P | + | 1 | 0.2 | + | 0.2 | 150' |
| P | + | 2 | 0.04 | + | 0.04 | 360' = 95% |
| P | + | 3 | 0.04 | + | 0.04 | 210' |
| P | + | 8 | 0.04 | + | 0.04 | 210' |
| P | + | 11 | 0.2 | + | 0.2 | 180' |
| P | + | 14 | 0.2 | + | 0.2 | 210' |
| P | + | 19 | 0.2 | + | 0.2 | 150' |
| P | + | 25 | 0.04 | + | 0.04 | 360' = 90% |
| P | + | 26 | 0.04 | + | 0.04 | 360' |
| P | + | 27 | 0.04 | + | 0.04 | 360' |
| P | + | 29 | 0.04 | + | 0.04 | 120' |
| P | + | 30 | 0.04 | + | 0.04 | 360' |
| P | + | 32 | 0.04 | + | 0.04 | 360' |
| P | + | 33 | 0.2 | + | 0.2 | 360' |
| P | + | 34 | 0.2 | + | 0.2 | 240' |
| P | + | 35 | 0.2 | + | 0.2 | 360' = 95% |
| Q | + | Piperonyl butoxide | 0.04 | + | 0.04 | 240' |
| Q | + | 3 | 0.04 | + | 0.04 | 210' |
| Q | + | 9 | 0.04 | + | 0.04 | 180' |
| Q | + | 10 | 0.04 | + | 0.04 | 150' |
| Q | + | 14 | 0.04 | + | 0.04 | 150' |
| Q | + | 16 | 0.04 | + | 0.04 | 180' |
| Q | + | 18 | 0.04 | + | 0.04 | 180' |
| Q | + | 19 | 0.04 | + | 0.04 | 210' |
| Q | + | 24 | 0.04 | + | 0.04 | 210' |
| R | + | Piperonyl butoxide | 1.0 | + | 1.0 | 360' = 95% |
| R | + | 9 | 1.0 | + | 1.0 | 105' |
| S | + | Piperonyl butoxide | 1.0 | + | 1.0 | 360' = 95% |
| S | + | 9 | 1.0 | + | 1.0 | 45' |
| S | + | 20 | 1.0 | + | 1.0 | 90' |
| T | + | Piperonyl butoxide | 0.2 | + | 0.2 | 360' = 50% |
| T | + | 8 | 0.2 | + | 0.2 | 120' |
| T | + | 10 | 0.2 | + | 0.2 | 120' |
| T | + | 11 | 0.2 | + | 0.2 | 105' |
| T | + | 14 | 0.2 | + | 0.2 | 240' |
| T | + | 18 | 0.2 | + | 0.2 | 240' |
| T | + | 24 | 0.2 | + | 0.2 | 210' |

TABLE 6-continued

LT 100 Test with *Musca domestica* (Weymanns strain), resistant to phosphoric acid esters

| | | | | | | |
|---|---|---|---|---|---|---|
| U | + | Piperonyl butoxide | 0.008 | + | 0.008 | 150' |
| U | + | 8 | 0.008 | + | 0.008 | 60' |
| U | + | 11 | 0.008 | + | 0.008 | 60' |
| U | + | 14 | 0.008 | + | 0.008 | 60' |
| U | + | 18 | 0.008 | + | 0.008 | 105' |
| U | + | 19 | 0.008 | + | 0.008 | 90' |
| U | + | 24 | 0.008 | + | 0.008 | 90' |
| V | + | Piperonyl butoxide | 0.04 | + | 0.04 | 360' = 70% |
| V | + | 3 | 0.04 | + | 0.04 | 210' |
| V | + | 8 | 0.04 | + | 0.04 | 210' |
| V | + | 9 | 0.04 | + | 0.04 | 150' |
| V | + | 10 | 0.04 | + | 0.04 | 150' |
| V | + | 11 | 0.04 | + | 0.04 | 210' |
| V | + | 18 | 0.04 | + | 0.04 | 240' |
| V | + | 19 | 0.04 | + | 0.04 | 210' |
| V | + | 24 | 0.04 | + | 0.04 | 210' |
| W | + | Piperonyl butoxide | 0.2 | + | 0.2 | 360' |
| W | + | 3 | 0.2 | + | 0.2 | 120' |
| W | + | 8 | 0.2 | + | 0.2 | 180' |
| W | + | 10 | 0.2 | + | 0.2 | 75' |
| W | + | 11 | 0.2 | + | 0.2 | 150' |
| W | + | 14 | 0.2 | + | 0.2 | 150' |
| W | + | 19 | 0.2 | + | 0.2 | 105' |
| W | + | 24 | 0.2 | + | 0.2 | 240' |
| X | + | Piperonyl butoxide | 1.0 | + | 1.0 | 360' = 85% |
| X | + | 9 | 1.0 | + | 1.0 | 75' |
| X | + | 11 | 1.0 | + | 1.0 | 150' |
| X | + | 14 | 1.0 | + | 1.0 | 240' |
| X | + | 16 | 1.0 | + | 1.0 | 150' |
| X | + | 18 | 1.0 | + | 1.0 | 105' |
| X | + | 19 | 1.0 | + | 1.0 | 120' |
| Y | + | Piperonyl butoxide | 1.0 | + | 1.0 | 360' |
| Y | + | 9 | 1.0 | + | 1.0 | 240' |
| Y | + | 16 | 1.0 | + | 1.0 | 240' |
| Y | + | 20 | 1.0 | + | 1.0 | 240' |
| Z | + | Piperonyl butoxide | 1.0 | + | 1.0 | 360' = 85% |
| Z | + | 9 | 1.0 | + | 1.0 | 210' |
| Z | + | 16 | 1.0 | + | 1.0 | 180' |
| Z | + | 20 | 1.0 | + | 1.0 | 240' |

EXAMPLE 18

$LT_{100}$ test

Test insects

*Blattella germanicca* ♀ ♀

*Tribolium confusum*

*Trogoderma granarium* 4. larvae

Solvent: Acetone

Solutions were prepared from the active compounds, synergistic agents and mixtures of active compounds and synergistic agents, and 2.5 ml of each solution were pipetted onto a respective filterpaper disc of 9.5 cm diameter in a Petri dish. The filterpaper absorbed the solution. The Petri dish was left standing open until the solvent had completely evaporated. 25 test insects were then introduced into each Petri dish, and the dish was covered with a glass lid.

The condition of the insects was checked continuously for up to 6 hours and thereafter again after 24, 48 and 72 hours. The time required for a 100% knock-down action was determined. If the $LT_{100}$ was not reached after 72 hours, the percentage of the test insects which had been knocked down was determined.

The concentrations of the active compounds, synergistic agents and mixtures, and their actions, can be seen from the table which follows.

TABLE 7

LT 100 Test with various pests

| Identifying letter of the active compound | Synergistic Agent No. | Pest | Active compound | | Synergistic Agent | LT 100 after minutes or hours |
|---|---|---|---|---|---|---|
| B | | Blattella germ. ♀ ♀ | 0.04 | | | 72 hrs = 80% |
| B | + Piperonyl butoxide | Blattella germ. ♀ ♀ | 0.04 | + | 0.04 | 105' |
| | 9 | Blattella germ. ♀ ♀ | | | 0.2 | 72 hrs = 20% |
| B | + 9 | Blattella germ. ♀ ♀ | 0.04 | + | 0.04 | 60' |
| | 16 | Blattella germ. ♀ ♀ | | | 1.0 | 72 hrs = 0% |
| B | + 16 | Blattella germ. ♀ ♀ | 0.04 | + | 0.04 | 75' |
| | 20 | Blattella germ. ♀ ♀ | | | 1.0 | 72 hrs = 60% |
| B | + 20 | Blattella germ. ♀ ♀ | 0.04 | + | 0.04 | 60' |
| P | | Blattella germ. ♀ ♀ | 1.0 | | | 72 hrs = 20% |
| P | + Piperonyl butoxide | Blattella germ. ♀ ♀ | 1.0 | + | 1.0 | 72 hrs = 0% |
| P | + 16 | Blattella germ. ♀ ♀ | 1.0 | + | 1.0 | 24 hrs |
| P | + 20 | Blattella germ. ♀ ♀ | 1.0 | + | 1.0 | 24 hrs |
| Y | | Blattella germ. ♀ ♀ | 0.2 | | | 360' |
| Y | + Piperonyl butoxide | Blattella germ. ♀ ♀ | 0.2 | + | 0.2 | 24 hrs |

TABLE 7-continued

LT 100 Test with various pests

| Identifying letter of the active compound | Synergistic Agent No. | Pest | Active compound | | Synergistic Agent | LT 100 after minutes or hours |
|---|---|---|---|---|---|---|
| Y | + 9 | Blattella germ. ♀♀ | 0.2 | + | 0.2 | 210' |
| Y | + 16 | Blattella germ. ♀♀ | 0.2 | + | 0.2 | 180' |
| Y | + 20 | Blattella germ. ♀♀ | 0.2 | + | 0.2 | 180' |
| A | | Tribolium confusum | 1.0 | | | 210' |
| A | + Piperonyl butoxide 9 | Tribolium confusum Tribolium confusum | 1.0 | + | 1.0 1.0 | 180' 72 hrs = 0% |
| A | + 9 16 | Tribolium confusum Tibolium confusum | 1.0 | + | 1.0 1.0 | 75' 72 hrs = 0% |
| A | + 16 20 | Tribolium confusum Tribolium confusum | 1.0 | + | 1.0 1.0 | 75' 72 hrs = 0% |
| A | + 20 | Tribolium confusum | 1.0 | + | 1.0 | 60' |
| A | | Trogoderma granarium 4. larvae | 1.0 | | | 72 hrs = 0% |
| A | + Piperonyl butoxide 9 | Trogoderma granarium 4. larvae Trogoderma granarium 4. larvae | 1.0 | + | 1.0 1.0 | 72 hrs = 20% 72 hrs = 0% |
| A | + 9 16 | Trogoderma granarium 4. larvae Trogoderma granarium 4. larvae | 0.2 | + | 0.2 1.0 | 24 hrs 72 hrs = 0% |
| A | + 16 20 | Trogoderma granarium 4. larvae Trogoderma granarium 4. larvae | 1.0 | + | 1.0 1.0 | 24 hrs 72 hrs = 0% |
| A | + 20 | Trogoderma granarium 4. larvae | 0.2 | + | 0.2 | 24 hrs |

It will be appreciated that the instant specification and examples are set forth by way of illustration and not limitation, and that various modifications and changes may be made without departing from the spirit and scope of the present invention.

What we claim is:

1. A phosphoric acid ester selected from the group consisting of

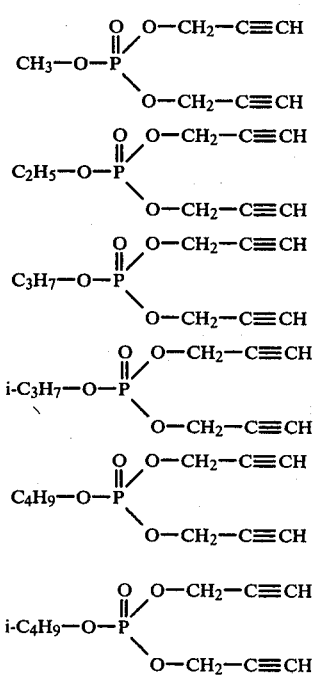

and

2. An ester according to claim 1, wherein such ester is

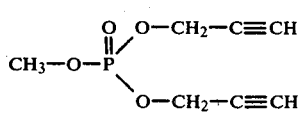

3. An ester according to claim 1, wherein such ester is

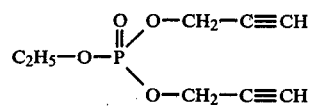

4. An ester according to claim 1, wherein such ester is

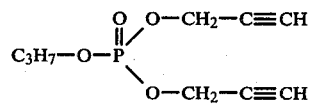

5. An ester according to claim 1, wherein such ester is

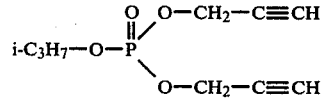

6. An ester according to claim 1, wherein such ester is

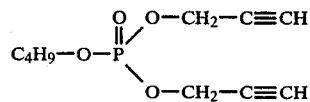

7. An ester according to claim 1, wherein such ester is

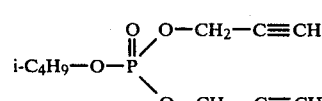

* * * * *

UNITED STATES PATENT AND TRADEMARK OFFICE
CERTIFICATE OF CORRECTION

PATENT NO. : 4,257,987
DATED : Mar. 24, 1981
INVENTOR(S) : Günter Arend et al

It is certified that error appears in the above-identified patent and that said Letters Patent are hereby corrected as shown below:

Title Page, Priority, Delete "June 8" and insert --June 18--.

Signed and Sealed this

Twenty-ninth Day of September 1981

[SEAL]

Attest:

Attesting Officer

GERALD J. MOSSINGHOFF

Commissioner of Patents and Trademarks